United States Patent [19]

Woodruff

[11] 4,316,382
[45] Feb. 23, 1982

[54] DETECTOR WITH INTERMITTENT FLOW

[75] Inventor: Terry A. Woodruff, Newark, Del.

[73] Assignee: Hewlett-Packard Company, Palo Alto, Calif.

[21] Appl. No.: 170,365

[22] Filed: Jul. 21, 1980

[51] Int. Cl.³ ............................................. G01N 27/18
[52] U.S. Cl. .................................................. 73/27 R
[58] Field of Search ........... 73/27 R, 23.1, 23, 864.81, 73/864.83; 422/89, 95, 98; 23/232 E

[56] References Cited

U.S. PATENT DOCUMENTS

| | | | |
|---|---|---|---|
| 2,255,551 | 9/1941 | Willenborg | 73/27 R |
| 4,185,490 | 1/1980 | Clouser et al. | 73/23.1 |
| 4,254,654 | 3/1981 | Clouser et al. | 73/27 R |

*Primary Examiner*—Stephen A. Kreitman
*Attorney, Agent, or Firm*—Donald N. Timbie

[57] ABSTRACT

Sample and reference fluids are made to alternately fill the volume of a concentration detector and remain there while measurements are made.

6 Claims, 9 Drawing Figures

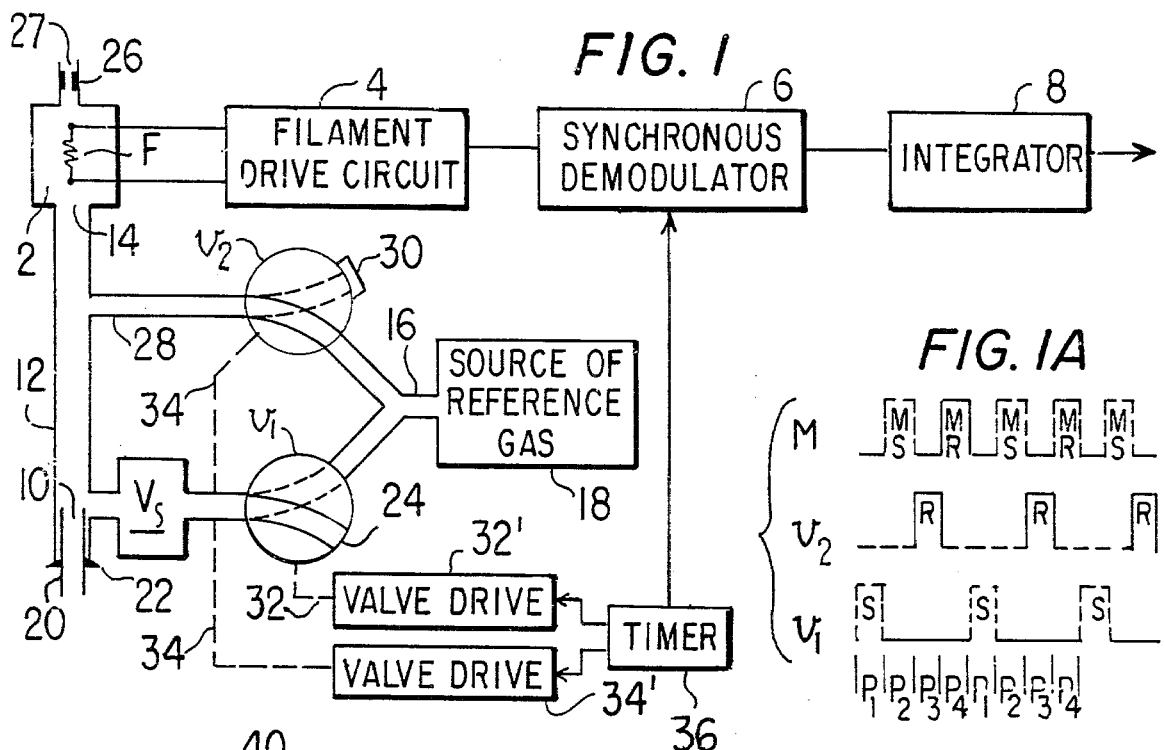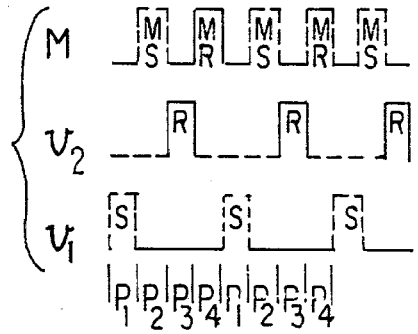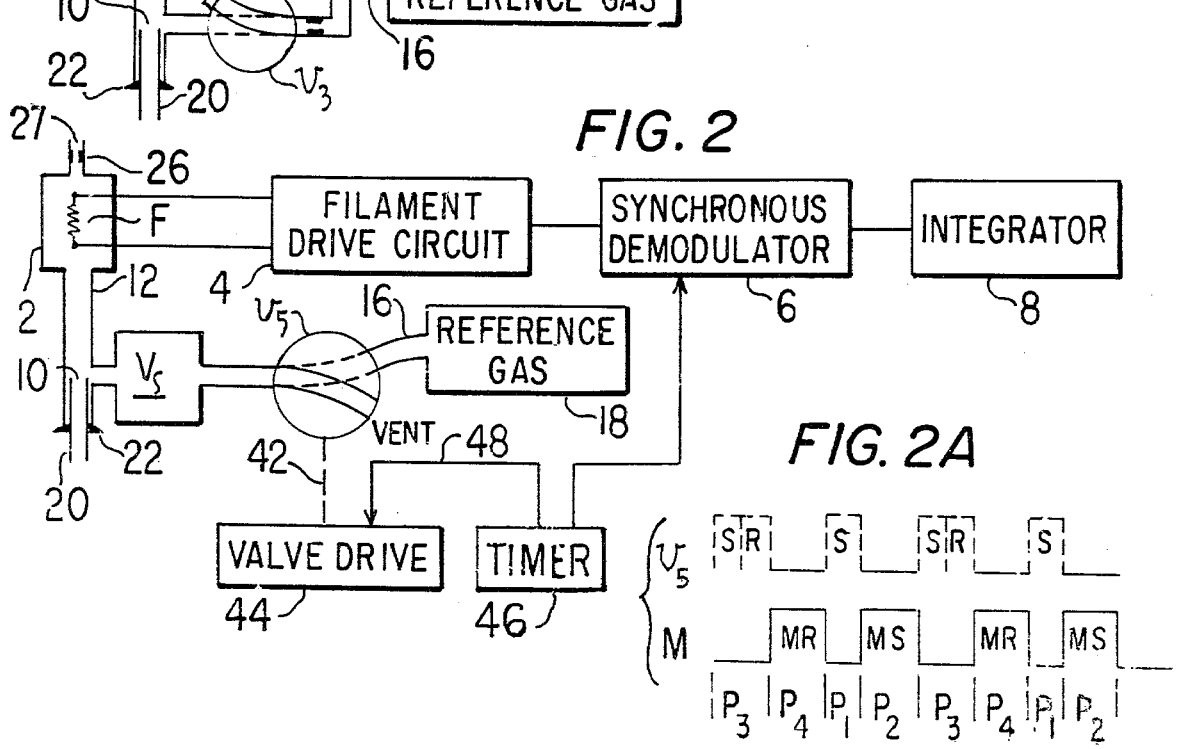

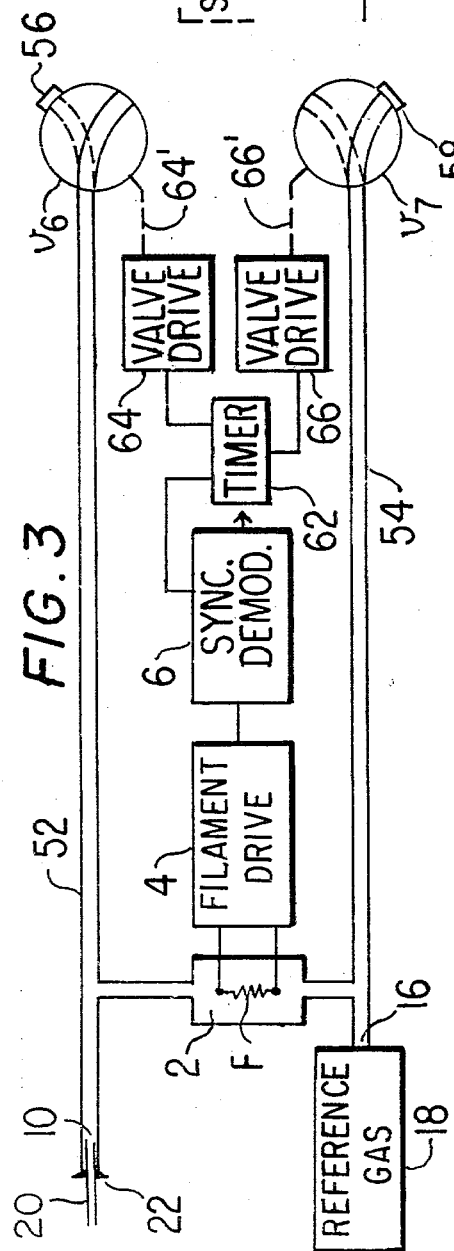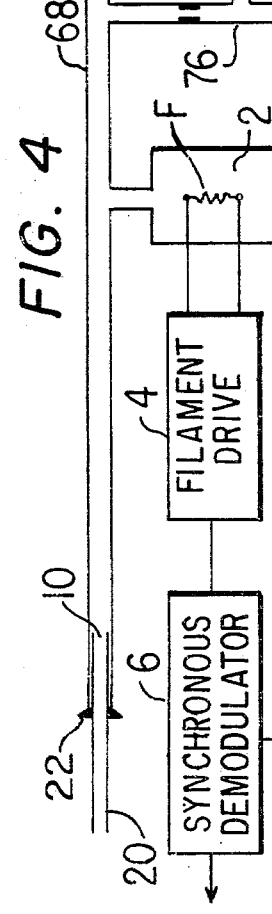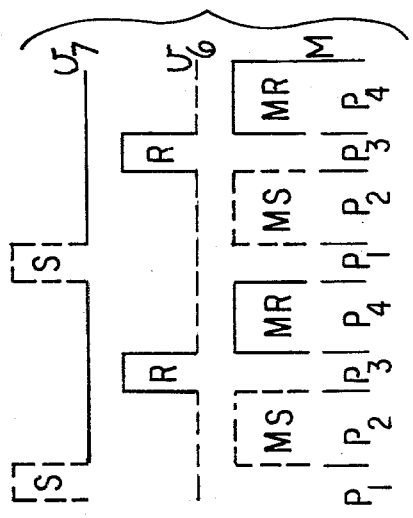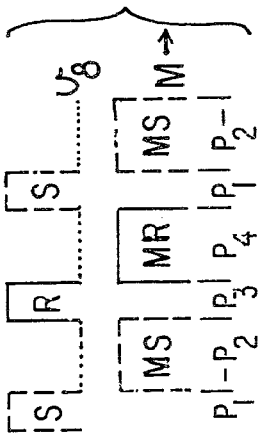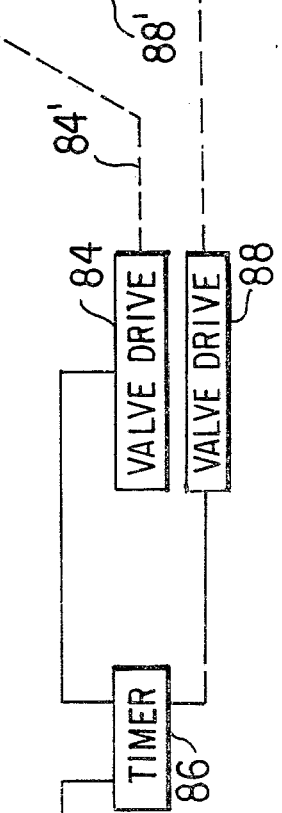

DETECTOR WITH INTERMITTENT FLOW

BACKGROUND OF THE INVENTION

This invention relates to improvements in systems that measure the quantity of solute in a flow of carrier fluid with a detector having a chamber into which the fluids may be injected and means for producing an electrical signal corresponding to the average value of a given characteristic of the fluids in the chamber. The combination of solute and carrier fluids is referred to as "sample fluid". When no solute is present in the sample fluid passing through the chamber, the electrical signal has what is known as a "baseline value", and when a concentration of solute is present in the sample fluid, the electrical signal changes from the baseline value to form a peak. The area between the peak and the baseline value corresponds to the quantity of the concentration of solute that has passed through the chamber. For various reasons, the baseline value drifts slowly with time so as to complicate measurement of the area.

This problem has been overcome by an invention of John S. Craven and David E. Clouser, set forth in their U.S. patent application entitled "Modulated Fluid Detector", Ser. No. 730,559, filed on Oct. 7, 1976, now U.S. Pat. No. 4,254,654. In accordance with that invention, sample fluid and reference fluid are alternately injected into the chamber of the detector a number of times during the peak in the electrical signal caused by the solute. The reference fluid may be carrier fluid or fluid that has the same value of the characteristic to which the detector responds as the carrier fluid, and that value is less or greater than the value of the characteristic of any solute to be analyzed. The electrical signal thus contains alternations betwen the value of the electrical peak signal referred to and the baseline value. The signal was synchronously detected so as to produce an output signal corresponding to the difference between the peak and the baseline values, and inasmuch as the baseline value is practically the same during each half of the alternation, it is eliminated by subtraction.

In applying the invention of the above patent application to a thermal conductivity or TC detector, alternate flows of sample gas, which is comprised of carrier gas having concentrations of the solute gas to be analyzed, and reference gas, which may be carrier gas or other gas having the same thermal conductivity, are made to pass through a single chamber in which a filament is suspended. The output signal of the detector is the voltage required to keep the filament at a constant temperature or resistance as it is cooled by heat flowing from the filament to the wall of the chamber. The output signal thus depends on the thermal conductivity of the gas in the chamber. When the chamber is filled with reference gas, the voltage has a baseline value; and when the chamber is filled with sample gas, the voltage has a value depending on the thermal conductivity of the sample gas—the greater its thermal conductivity, the greater is the flow of heat from the suspended filament to the wall of the chamber and the greater, therefore, is the voltage output of the detector.

As originally conceived, the flow rates of the sample and reference gases were sufficiently large that the chamber was filled with sample gas during nearly all of one half-cycle of the alternate flow and with reference gas during nearly all of the next half-cycle. The synchronous detector was operated in phase with the alternation of flow of sample and reference gases so as to produce an output signal corresponding to the difference between the detector signal occurring when the chamber was full of sample gas and the detector signal occurring when the chamber was full of reference gas. Whereas this virtually eliminated the effects of variation in the value of the baseline, it was found that flow noise was introduced into the output signal whenever there was a change in the difference between the flows of sample and reference gases. This problem was met by another invention of John S. Craven and David E. Clouser set forth in their U.S. Pat. No. 4,185,490 in which the flows of sample and reference gas were such that each gas just filled the chamber at the end of its half-cycle of flow so as to produce a detector signal having a maximum value at the end of one half-cycle and a minimum value at the end of the other half-cycle. In addition, the synchronous detector was operated 90° out of phase with the gas flow so as to derive an output signal corresponding to the difference between the maximum and minimum values.

Whereas this type of operation reduces the flow noise to a minimum, it cuts the amount of sample gas introduced into the chamber in half and reduces the signal that can be attained by a like amount. Furthermore, as long as the gases are flowing through the chamber when a measurement is being taken by the synchronous detector, differences in heat capacities or the diffusion coefficients of the sample and references gases may have adverse effects on the measurements.

BRIEF DESCRIPTION OF THE INVENTION

In accordance with this invention, means are provided for conducting the sample gas and reference gas to the cell of the TC detector at different times and holding them there so that they are not flowing, or flowing at a relatively slow rate, while the synchronous demodulator is performing its measuring function. This avoids disturbance due to the sample thermal capacity resulting from the energy it takes to heat the sample gas which is a different thing from the thermal conductivity of the gas. It also eliminates the problem of flow noise that was addressed in the U.S. patent referred to. Also avoided are disturbances due to momentary changes in flow or pressure that are especially bothersome when large amounts of sample chemicals are eluting from the column of a detector supplying sample gas to the detector. These disturbances are typically negative peaks produced in response to a change in the elution rate from the column as the sample goes from a liquid or absorbed state to a gas phase. In attaining these advantages as well as others not enumerated, the detector system of this invention has better sensitivity. Although not necessary, the sensitivity may be increased by storing the sample gas eluting from the column as described in my U.S. patent application entitled "Modulated Detector", Ser. No. 167,856 and filed on 07/14/80.

BRIEF DESCRIPTION OF THE DRAWINGS

FIG. 1 illustrates a thermal conductivity detector system that utilizes two valves to control the flow of sample and reference gas in accordance with the invention and incorporates a storage volume so as to improve the signal-to-noise ratio when operating with low flow rate columns, including capillary columns, as set forth in my copending U.S. patent application referred to above;

FIG. 1A includes graphs used in explaining the operation of FIG. 1;

FIG. 1B illustrates another arrangement of two valves that may be substituted for the valves of FIG. 1;

FIG. 2 illustrates a thermal conductivity detector system that utilizes a single valve to control the flows of sample and reference gas in accordance with this invention and incorporates a storage volume so as to improve the signal-to-noise ratio when operating with low flow rate columns, including capillary columns, as set forth in my copending U.S. patent application referred to above;

FIG. 2A includes graphs used in explaining the operation of FIG. 2;

FIG. 3 illustrates a thermal conductivity system having two valves for controlling the fluid flow in accordance with this invention;

FIG. 3A includes graphs used in explaining the operation of FIG. 3;

FIG. 4 illustrates a thermal conductivity system that utilizes a single valve to control the fluid flow in accordance with this invention in such manner that neither sample nor reference gas flows through it; and FIG. 4A includes graphs used in explaining the operation of FIG. 4.

DETAILED DESCRIPTION OF THE INVENTION

Reference is now made to the thermal conductivity system of FIG. 1 wherein a thermal conductivity detector is comprised of a chamber 2 having a filament F suspended therein that is connected to a filament drive circuit 4. A voltage that is required to keep the filament F at a constant temperature is developed by the filament drive circuit 4 and applied to synchronous demodulator 6. An integrator 8 is coupled to the output of the synchronous demodulator 6 so as to derive an output signal corresponding to the areas between the signal peaks and the baseline value that represent the quantities of the respective solutes.

A fluid control means is provided for causing sample fluid, in this case sample gas, to flow into the chamber 2 during spaced first period of time $P_1$ by the pulses S of the graph $v_1$ of FIG. 1A and to remain in the chamber 2 during following second periods of time $P_2$. The fluid control means is comprised of a first input port 10 to which sample fluid may be applied, a tube 12 connected between the input port 10 and a fluid entrance 14 of the chamber 2 and a storage volume $V_S$ and a first valve $v_1$ connected in the order named between the first fluid input 10 and a second fluid input 16 to which reference gas from a pressurized source 18 may be applied. Sample gas may be applied to the first input port 10 by a column 20 that is sealed to the tube 12 by ferrules 22. The first input port 10 is the cross-section of the tube 12 that is at the end of the column 20.

When the valve $v_1$ is in the solid-line position during periods $P_2$, $P_3$ and $P_4$, shown in the graph $v_1$ of FIG. 1A, the storage volume $V_S$ is connected to a vent 24 so that sample gas from the column 20 can flow into the storage volume $V_S$. This is the path nearly all the gas will follow because of a restrictor 26 contained in the vent outlet of the chamber 2. The amount of sample gas that enters the chamber 2 is negligible. During the next period $P_1$, the valve $v_1$ is placed in its dashed-line position as indicated by the dashed pulses S of the graph $v_1$ so as to connect the first input port 10 to the second input port 16. The reference gas forces the sample gas stored in the volume $V_S$ into the chamber 2 of the detector. At the end of $P_1$ when the last sample gas enters the chamber 2, the valve $v_1$ reverts to its solid-line position so that the sample gas remains in the chamber 2 during the period $P_2$.

A fluid control means is also provided for causing reference gas to flow into the chamber 2 during period $P_3$ of FIG. 1A and to remain in the chamber 2 during the periods $P_4$. The fluid control means is comprised of a valve $v_2$ connected by a tube 28 between the fluid entrance 14 of the chamber 2 and the second fluid input port 16. During the periods $P_1$ and $P_2$ of the graph $v_2$, the valve $v_2$ is in its dashed-line position so that the tube 28 is connected to a stop 30 and thus does not interfere with the injection of the sample gas into the chamber 2 during periods $P_1$ and retaining it there during periods $P_2$.

When in its solid-line position during periods $P_3$, the valve $v_2$ connects the fluid entrance 14 to the second input port 16 so that reference gas forces the sample gas from the chamber 2 as indicated by the pulses R. At the end of a period $P_3$, the valve $v_2$ reverts to its dashed line position so that the reference gas remains in the chamber 2. During periods $P_3$ and $P_4$, the valve $v_1$ is in its solid-line position as previously described so that it does not interfere with the passage of reference gas into the chamber 2 during periods $P_3$ or with its retention there during the periods $P_4$.

The valves $v_1$ and $v_2$ are respectively placed in their respective positions by mechanical couplings indicated by dashed lines 32 and 34 that are actuated by valve drive means 32' and 34' under the control of a timer 36. The timer 36 outputs pulses like the pulses S of the graph $v_1$ to the valve drive 32' so as to move the valve $v_1$ to its dashed-line position and outputs pulses like the pulses R of the graph $v_2$ to the valve drive 34' so as to move the valve $v_2$ to its solid-line position.

Measurement of the output of the filament drive circuit by the synchronous detector 6 during the periods $P_2$ and $P_4$ is accomplished by providing enabling pulses during these periods such as indicated by the graph M of FIG. 1A from the timer 36. The synchronous demodulator 6 derives an output signal corresponding to the difference between the voltage produced by the filament drive circuit during each period $P_2$ when the chamber 2 is filled with sample gas and the voltage it produces during each following period $P_4$ when the chamber 2 is filled with reference gas.

In FIG. 1B, which shows an alternative control mechanism for the sample and reference gases, parts corresponding to those of FIG. 1 are indicated by the same numerals. The structure of FIG. 1B can be incorporated into the structure of FIG. 1 by inserting the top of the tube 12 into the field entrance 14 of the chamber 2. Valves $v_3$ and $v_4$ are respectively connected between the first fluid input port 10 and the fluid entrance 14 to the second fluid input port 16. The valves $v_3$ and $v_4$ are respectively operated in the same way as the valves $v_1$ and $v_2$ of FIG. 1 as indicated by the graphs $v_1$ and $v_2$ of FIG. 1A. Thus, a first fluid control means for causing sample gas to flow into the chamber 2 during spaced periods $P_1$ and to remain there during periods $P_2$ is the valve $v_3$. In this embodiment, the storage volume indicated by $V_S'$ is the portion of the tube 12 between the first input port 10 and the fluid entrance 14 of the chamber 2. During periods $P_2$, $P_3$ and $P_4$, the valve $v_3$ is in its solid-line position so that it connects the second input port 16 to a stop, or if desired to a vent, and sample gas flows from the column 20 into the storage volume $V_S'$. The flow of sample gas to the chamber 2 is negligible. During the periods $P_1$, the valve $v_3$ is in its dashed-line position so as to connect the first input port 10 to the second input port 16 and, as indicated by the pulses S of the graph $v_1$ of FIG. 1A, the reference gas forces the stored sample gas into the chamber 2 of FIG. 1. The valve $v_3$ then reverts to its solid-line position so as to permit the sample gas to remain in the chamber 2 during the following periods $P_2$ when it is measured by the synchronous detector 6 as indicated by the pulses MS of the graph M of FIG. 1A. During periods $P_1$ and $P_2$, the valve $v_4$ is in its dashed-line position so as to connect the second fluid input port 16 to a stop 40, or to a vent if desired, and not interfere with the functions just described in connection with the valve $v_3$.

A second fluid control means for causing reference gas to flow into the chamber 2 during spaced periods $P_3$ and to remain there during periods $P_4$ is the valve $v_4$. During the periods $P_3$, the valve $v_4$ is in its solid-line position as indicated by the pulses S of the graph v of FIG. 1A so that reference gas flows through it to the fluid entrance 14 and pushes the sample gas in the chamber 2 out of the fluid outlet 27. The valve $v_4$ then reverts to its dashed-line position so that the reference gas remains in the chamber 2 during the period $P_4$. During the periods $P_3$ and $P_4$, the valve $v_3$ is in its solid-line position so as not to interfere with the functions performed by the valve $v_4$.

Reference is now made to FIG. 2 illustrating an embodiment of the invention wherein a single valve is used to control the flow of both sample gas and reference gas. Those parts corresponding to FIG. 1 are indicated by the same numerals and will not be further described. The storage volume $V_S$ and a valve $v_5$ are connected in the order named between the first fluid input port 10 and the second fluid input port 16. During period $P_4$, when $v_5$ is in its solid-line position, also indicated by a solid line in graph $v_5$ of FIG. 2A, the valve $v_5$ connects the storage volume $V_S$ to a vent. The period $P_4$ is long enough to permit sample gas to fill $V_S$. During first periods $P_1$, the valve $v_5$ is in its dashed-line position so as to connect the first inlet port 10 to the second inlet port 16 and permit the pressurized reference gas to force the sample gas stored in $V_S$ into the chamber 2 as indicated by the pulses S. The sample gas remains in the chamber 2 during the periods $P_2$ when $v_5$ reverts to its solid-line position and sample gas once again fills $V_S$. Then, during periods $P_3$, the valve $v_5$ is positioned in its dashed-line position so that once again reference gas forces the sample gas in $V_S$ into the chamber 2 in the first part of the period $P_3$ as indicated by the letter S in the graph $v_5$. Periods $P_3$ are longer than the periods $P_1$ so that during their latter part the reference gas pushes the sample gas out of the port 27 and leaves the chamber 2 filled with reference gas as indicated by the letter R. Following this, during periods $P_4$ when sample gas is filling $V_S$, the reference gas remains in the chamber 2.

Positioning of the valve $v_5$ may be effected by a mechanical linkage represented by the dashed line 42 that is moved by a valve drive 44. A timer 46 such as a Johnson counter provides pulses during the periods $P_1$ via a lead 48 to the valve drive 44 so as to cause it to move the valve $v_5$ to its dashed-line position; and during periods $P_3$, the timer 46 provides a pulse of longer duration to the valve drive 44.

Measurement of the voltage at the output of the filament drive circuit 4 during the periods $P_2$, when the sample gas is stationary in the chamber 2, is effected by applying pulses MS of the graph M that occur during the periods $P_2$ from the timer 46 to the synchronous demodulator 6. Measurement of the voltage at the output of the filament drive circuit 4 during the periods $P_4$ when reference gas is stationary in the chamber 2 is effected by applying pulses MR of the graph M that occur during the perids $P_4$ from the timer 46 to the synchronous demodulator 6.

Because the embodiments of the invention illustrated in FIGS. 1, 1B and 2 have a storage volume $V_S$, they are especially advantageous when the source of sample gas has a slow flow such as that from a capillary column for reasons set forth in my U.S. patent application entitled "Modulated Detector", Ser. No. 167,856 filed on July 14, 1980.

FIG. 3 illustrates an application of this invention to situations where the flow of sample gas is such as to fill the chamber during the first spaced periods, e.g., when a packed column is used. The components of FIG. 3 that perform the same function as in FIG. 1 are designated by the same numerals and need not be further described.

In this particular embodiment, the chamber 2 of the TC detector is connected between the first input port 10 to which sample gas is applied and the second input port 16 to which pressurized reference gas from a source 18 is applied. A tube 52 connects the first input port 10 and one end of the chamber 2 to a valve $v_6$, and a tube 54 connects the second input port 16 and the other end of the chamber 2 to a valve $v_7$.

The valve $v_7$ is in its solid-line position closing off the tube 54 only during periods $P_3$ as indicated by the solid pulses R of the graph $v_7$ of FIG. 3A, and the valve $v_6$ is in its dashed-line position closing the tube 52 only during the periods $P_1$ as indicated by the dashed-line pulses S of the graph $v_6$ of FIG. 3A. When the valve $v_6$ is in its solid-line position, the tube 52 is connected to a vent; and when the valve $v_7$ is in its dashed-line position, the tube 54 is also connected to a vent. Thus, during the periods $P_1$, sample gas flows into the chamber 2 and it remains there during the periods $P_2$. In the periods $P_3$, reference gas flows into the chamber 2 and remains there during the periods $P_4$. Operation of the valves $v_6$ and $v_7$ in this manner is achieved by applying pulses from a timer 62 to a valve drive means 64 during the periods $P_1$ and by applying high state pulses from the timer 62 to a valve drive means 66 during the periods $P_3$. The valve drive means 64 and 66 are respectively coupled to the valves $v_6$ and $v_7$ by mechanical activating means indicated by the dashed lines 64' and 66'.

FIG. 4 illustrates a system utilizing a thermal conductivity detector in accordance with the invention in which a single valve is used to control the flows of sample and reference gas to the chamber of the detector in such manner that the sample and reference gases do not enter the valve. Components corresponding to those of FIG. 1 are indicated by the same numerals and are not further described. The first input port 10 is connected via a tube 68 to a valve $v_8$, and the second input port 16 is connected via a tube 70 to the valve $v_8$. In its dashed-line position, the valve $v_8$ connects the tube 68 to a source 72 of pressurized switching gas; and in its solid-line position, it connects the tube 70 to the source 72. In its dotted position, the valve $v_8$ connects the source 72 to a stop 74 or to a vent. As in FIG. 3, the detector chamber 2 is connected between the tubes 68 and 70. A tube 76 is connected between the tubes 68 and 70 at points intermediate to their connection to the chamber 2 and the valve v8. At its center, the tube 76 is connected to a tube 78 that leads to a vent and restrictors 80 and 82 are mounted in the tube 76 on either side of its connection to the tube 78.

When the valve $v_8$ is in its dashed position, switching gas is introduced into the tube 68 with such pressure as to block the flow of sample gas to the tube 76, thereby causing the sample gas to pass through the detector chamber 2, toward the valve $v_8$ along the tube 70 and to the vent tube 78 via the tube 76. When the valve $v_8$ is in its solid-line position, switching gas is applied to the tube 70 with sufficient pressure to prevent reference gas from flowing to the tube 76. Thus, if as indicated in the graph $v_8$ of FIG. 4A the valve $v_8$ is in its dashed-line position only during the periods $P_1$ as indicated by the dashed pulses S, in its solid-line position only during periods $P_3$ as indicated by the solid-line pulses R, and in its dotted-line position during the periods $P_2$ and $P_4$, the sample gas will enter the chamber 2 during periods $P_1$ and remain there during the periods $P_2$; and the reference gas will enter the chamber 2 during the periods $P_3$ and remain there during the periods $P_4$. The valve can be moved to the required position by applying pulses to a valve drive means 84 from a timer 86 during the periods $P_1$ so as to move the valve $v_8$ from its neutral position to its dashed-line position via a mechanical coupling indicated by a dashed line 84' and by applying pulses from the timer 86 to a valve drive 88 during periods $P_3$ that moves the valve $v_8$ from its neutral position to its solid-line position via a mechanical coupling indicated by a dashed line 88'.

Measurement of the signal provided by the filament drive 4 during the periods $P_2$ when the sample gas is stationary in the detector chamber 2 is effected by applying the pulses from the timer 86 to the synchronousdetector 6 during the periods $P_2$ as indicated by the pulses MS of the graph M of FIG. 4A; and measurement of the signal provided by the filament drive 4 during periods $P_4$ when the reference gas is stationary in the detector chamber 2 is effected by applying pulses from the timer 86 to the synchronous detector 6 during the periods $P_4$ as indicated by the pulses MR in the graph M of FIG. 4A.

What is claimed is:

1. A concentration detector system including means for modulating the respective flows of sample and reference fluids through the detector, comprising
    a detector having a chamber and means for producing an electrical signal corresponding to the value of a given characteristic of material contained in said chamber,
    first fluid control means causing sample fluid, when present, to flow into a fluid entrance of said chamber during spaced first periods of time and to remain in said chamber during second periods of time respectively occurring after said first periods,
    second fluid control means causing reference fluid, when present, to flow into said chamber during third periods of time that follow said second periods of time and to remain in said chamber during fourth periods of time that follow said third periods, the first, second, third and fourth periods occurring in repeated sequence, and
    a synchronous detector coupled to receive the electrical signals produced by said detector for deriving a signal corresponding to the difference between the amplitude of the electrical signals produced during said third and fourth periods of time.

2. A concentration detector system as set forth in claim 1 wherein
    said first fluid control means includes a storage volume and a first valve connected in the order named between said first input port and said second input port, said first valve connecting said storage volume to said second input port when in a first position and to a vent when in a second position, there being a fluid connection between said first input port and said fluid entrance of said detector chamber, and means for causing said first valve to be in said first position only during said first periods of time and in said second position only during said second periods of time,
    said second fluid control means includes a second valve mounted between said second input port and said fluid entrance of said detector, said second valve connecting said fluid entrance to said second input port when in a first position and to a stop when in a second position and means for causing said second valve to be in said first position only during said third periods of time and in said second position only during said fourth periods of time.

3. A concentration detector system as set forth in claim 1 wherein
    said first fluid control means includes a valve connecting said first input port to said second input port when in a first position and connecting said second input port to a stop when in a second position,
    said second fluid control means includes a valve connecting said second input port to a vent when in a first position and connecting said second input port to said fluid entrance of said detector chamber when in a second position, and
    means defining a storage volume connected between said first inlet port and said fluid entrance of said detector chamber.

4. A concentration detector system as set forth in claim 1 wherein said first fluid control means is comprised of
    a first fluid input port to which sample fluid may be applied, said first fluid input port being connected to said chamber,
    a second input port to which reference fluid may be applied,
    a valve,
    a storage volume connected between said first input port and said valve, and
    means for positioning said valve in a first position so as to connect said storagevolume to said second input port during said first periods of time so that sample fluid in said storage volume is transferred to said chamber and for positioning said valve in a second position so as to connect said storage volume to a vent during said second periods of time whereby said sample fluid remains in said chamber,
    said second fluid control means including in addition means for positioning said valve in said second position during said third periods of time that are long enough to permit reference gas to force all of the sample fluid contained in said storage volume through said chamber and to fill said chamber with reference gas, and for positioning said valve in said second position during said fourth periods of time so that the reference gas remains in said chamber.

5. A concentration detector system as set forth in claim 1 wherein said first and second fluid control means are comprised of
- a first input to which sample fluid may be applied,
- a first tube having one end connected to said first input,
- a first valve connected to the other end of said first tube, said first valve blocking the said other end of said first tube when in a first position and connecting the said other end of said first tube to atmosphere when in a second position,
- a second input to which reference fluid may be applied,
- a second tube having one end connected to said second input,
- a second valve connected to the other end of said second tube, said second valve blocking said other end of said second tube when in a first position and connecting said other end of said second tube to atmosphere when in a second position,
- means connecting said chamber between intermediate points of said first and second tubes,
- means placing said first valve in said first position and said second valve in said second position during said first periods of time,
- means for placing said first and second valves in said first positions during said second periods of time,
- means placing said first valve in said second position and said second valve in said first position during said third periods of time, and
- means for placing said first and second valves in said first positions during said fourth periods of time.

6. A concentration detector system as set forth in claim 1 wherein said first and second fluid control systems are comprised of
- a first input to which sample fluid may be applied,
- a valve having an input to which switching gas may be applied and first, second and third outputs to which said input is selectively connected when said valve is in first, second and third positions respectively,
- a first tube connected between said first input and said first output of said valve,
- a second input to which reference fluid may be applied,
- a second tube connected between said second input and said second output of said valve,
- means connecting said chamber between intermediate points of said first and second tubes,
- a third tube connected between a vent and a point of said first tube that is between said intermediate point and said first output of said valve,
- a fourth tube connected between a vent and a point of said second tube that is between said intermediate point and said second output of said valve, and
- means for positioning said valve in said first position during said first periods, in said second position during said third periods, and in said third position during said second and fourth periods.

* * * * *